United States Patent
Osman

(10) Patent No.: US 8,454,676 B1
(45) Date of Patent: Jun. 4, 2013

(54) TRANSITION MATCHING STENT

(75) Inventor: Karim Said Osman, Mountain View, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 2027 days.

(21) Appl. No.: 10/762,069

(22) Filed: Jan. 20, 2004

(51) Int. Cl.
*A61F 2/06* (2006.01)

(52) U.S. Cl.
USPC ........................................................ 623/1.15

(58) Field of Classification Search
USPC .................... 623/1.11–1.19, 1.32, 1.49–1.54, 623/1.2, 1.3, 1.31, 1.4
See application file for complete search history.

(56) References Cited

U.S. PATENT DOCUMENTS

| | | | |
|---|---|---|---|
| 6,106,548 A * | 8/2000 | Roubin et al. | 623/1.15 |
| 6,676,697 B1 * | 1/2004 | Richter | 623/1.16 |
| 6,846,323 B2 * | 1/2005 | Yip et al. | 623/1.16 |
| 6,887,264 B2 * | 5/2005 | Penn et al. | 623/1.15 |
| 7,112,216 B2 * | 9/2006 | Gregorich | 623/1.15 |
| 2002/0095208 A1 * | 7/2002 | Gregorich et al. | 623/1.15 |
| 2002/0198593 A1 * | 12/2002 | Gomez et al. | 623/1.16 |
| 2003/0074056 A1 * | 4/2003 | Killion et al. | 623/1.16 |
| 2004/0088043 A1 * | 5/2004 | Klein | 623/1.16 |

* cited by examiner

*Primary Examiner* — Thomas McEvoy
(74) *Attorney, Agent, or Firm* — Fulwider Patton LLP

(57) ABSTRACT

The bending flexibility profile of a stent closely matches the flexibilities of the stent delivery system on either side of the stent. In one embodiment, a stent has a longitudinal axis and at least one link attaching each ring to an adjacent ring. The links closest to the stent end rings have the greatest bending flexibility and the links closest to the center of the stent have the least bending flexibility.

10 Claims, 9 Drawing Sheets

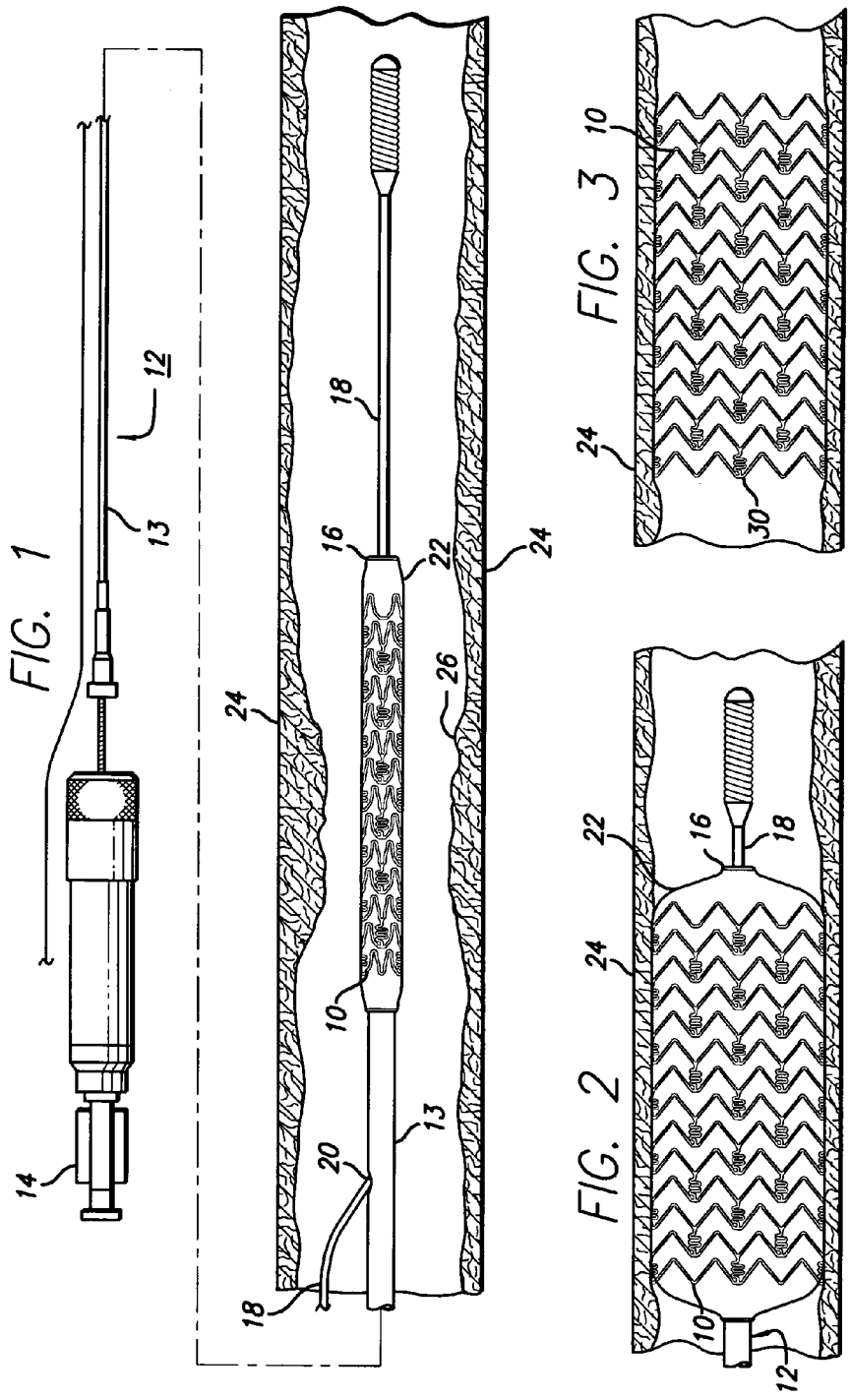

TRANSITION MATCHING STENT

BACKGROUND OF THE INVENTION

The invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular shaped devices which function to hold open a segment of the blood vessel or other body lumens such as a coronary artery. They also are suitable for use to support and hold back a dissected arterial lining that can occlude the fluid passageway. At present, there are numerous commercial stents being marketed throughout the world. For example, the prior art stents depicted in FIGS. 1-4 have multiple cylindrical rings connected by one or more undulating links.

FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guidewire by any of the well known methods of an over-the-wire system (not shown) or a well known rapid exchange catheter system, such as the one shown in FIG. 1.

Catheter assembly 12 as depicted in FIG. 1 is of the well known rapid exchange type which includes an RX port 20 where the guidewire 18 will execute the catheter. The distal end of the guidewire 18 exits the catheter distal end 16 so that the catheter advances along the guidewire on a section of the catheter between the RX port 20 and the catheter distal 16. As is known in the art, the guidewire lumen which receives the guidewire is sized for receiving various diameter guidewires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

In a typical procedure to implant prior art stent 10, the guidewire 18 is advanced through the patient's vascular system by well known methods so that the distal end of the guidewire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guidewire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system.

The guidewire typically is left in the lumen for post-dilation procedures, if any, and subsequently is withdrawn from the patient vascular system. As depicted in FIGS. 2 and 3, the balloon is fully inflated with the prior art stent expanded and pressed against the vessel wall and, in FIG. 3, the implanted stent remains in the vessel after the balloon has been deflated and the catheter assembly and guidewire have been withdrawn from the patient.

FIG. 4 illustrates the prior art stent 10 in some detail. The undulating portion 27 of the links 28 are positioned between two struts 29A/29B. The links 28 all have the same undulating pattern on the strut. Consequently, the bending stiffness profile of the stent is substantially constant along the length of the stent.

Typically, stent design has focused on maximizing the flexibility of the stent. However, less attention has been paid to the sharp change in flexibility of the stent delivery system at the beginning and ending points of the stent. FIG. 5 illustrates a stiffness profile of a typical traditional stent delivery system. As FIG. 5 illustrates, the stiffness of the system sharply increases at the one end of the stent, with very little transition in stiffness between the stent and the portion of the stent delivery system immediately adjacent the stent. What is desired is a stent delivery system having a stent that smoothes the stiffness transition in the stent delivery system at the ends of the stent itself.

SUMMARY OF THE INVENTION

A flexible intravascular stent for use in a body lumen has a plurality of rings interconnected to form a stent. The stent has a first end portion, a center portion, and a second end portion. At least one link attaches each ring to an adjacent ring. To make the stent better match the stiffness profile of the stent delivery system, at least one of the first and second end portions has more bending flexibility than the center portion.

In one embodiment, the stent has a longitudinal axis, and the at least one link attaching each ring to an adjacent ring has an undulating link having a curved portion extending transverse to the stent's longitudinal axis. To make the center stiffer than at least one of the two ends, the curved portion of the links in the center section may have a curvature that is different (e.g. having different diameters) than the diameter of the curved portion of the links in at least one of the first end portion and the second end portion.

As an alternative, the links in at least one of the first end and the second end portions may be made of a stiffer, different material than the material of the links in the center portion. The links may be made of, for example, polymer material, with the polymer at the first and/or second end of the stent being more stiff than the polymer at the center portion. As another alternative, the links in at least one of the first end and the second end portions may be thinner, in terms of thickness or width, than the links in the center portion.

As a further alternative, at least some of the links may comprise coils, the coils of links in at least one of the first and second end portions being more flexible in bending than the coils in the center portion. Alternatively, at least some of the links may comprise nonlinearities, at least one of the first end portion and the second end portion including more nonlinearities per link than in the center portion. For example, the links may include undulating (e.g., bends, loops, arcs, saw tooth, square wave, sinusoidal, etc.) portions, the undulating portions on at least one of the first and second end portions being more flexible in bending than the sinusoidal portions in the center portion.

In one embodiment, both the first and second end portions have more bending flexibility than the center portion. In another embodiment, the bending stiffness of the links gradually increases from at least one of the first and second end portions to the center portion.

These and other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a prior art stent mounted on a rapid exchange delivery catheter and positioned within an artery;

FIG. 2 is an elevational view, partially in section, similar to that shown in FIG. 1 wherein the prior art stent is expanded within the artery so that the stent embeds within the arterial wall;

FIG. 3 is an elevational view, partially in section, showing the expanded prior art stent implanted within the artery after withdrawal of the rapid exchange delivery catheter.

DETAILED DESCRIPTION OF THE PREFERRED EMBODIMENTS

Figure 6A:
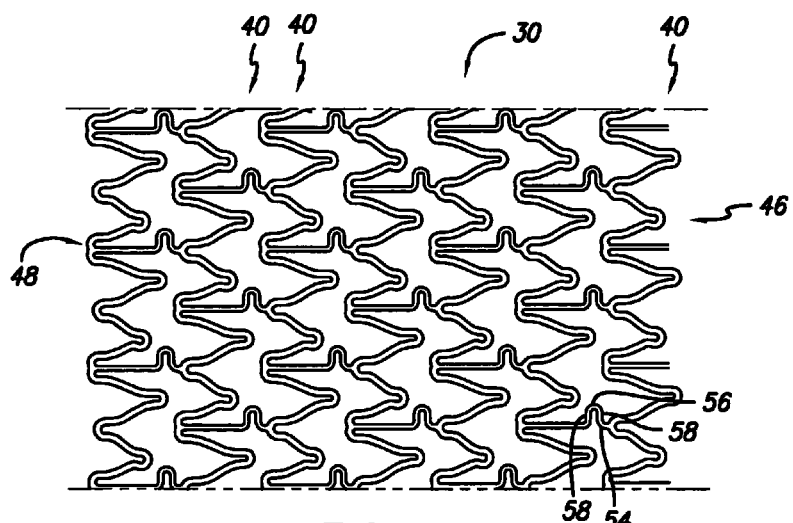
FIGS. 6A-6C are views of another stent which illustrates a pattern of rings and links.
Figure 6B:
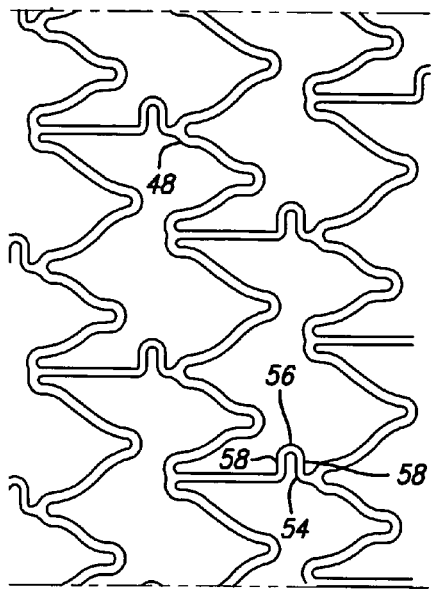
Figure 6C:
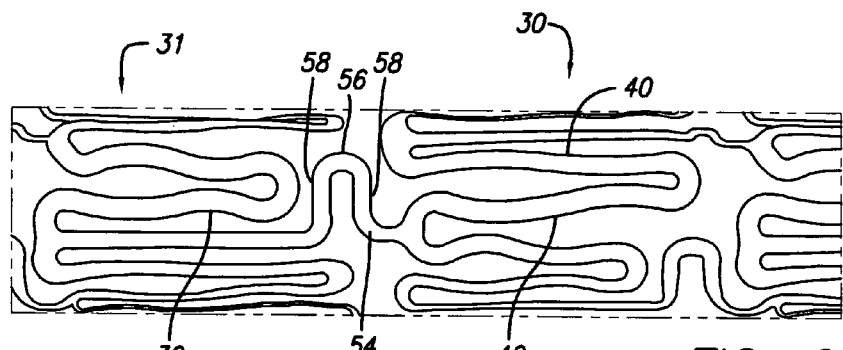

Considering now one existing stent design in some detail, FIGS. 6A-C illustrate another type of stent, as described in U.S. Pat. No. 6,629,994. FIGS. 6A-C depict stent 30 in various configurations. Referring to FIG. 6A, for example stent 30 is shown in a flattened condition so that the pattern can be clearly viewed, even though the stent is in a cylindrical form in use, such as shown in FIG. 6C. The stent is typically formed from a tubular member, although, it can be formed from a flat sheet such as shown in FIG. 6A and rolled into a cylindrical configuration as shown in FIG. 6C.

As shown in FIGS. 6A-6C, stent 30 is made up of a plurality of cylindrical rings 40 which extend circumferentially around the stent when it is in a tubular form (see FIG. 6C). Each cylindrical ring 40 has a cylindrical ring proximal end 46 and a cylindrical ring distal end 48. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 40 defines a cylindrical plane 50 (FIG. 6C) which is a plane defined by the proximal and distal ends 46,48 of the ring and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

Undulating link 54 is positioned within cylindrical plane 50. The undulating links connect one cylindrical ring 40 to an adjacent cylindrical ring 40 and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction. With the straight portions being substantially perpendicular to the stent longitudinal axis, the undulating link acts much like a hinge at the curved portion to provide flexibility.

Figure 4:
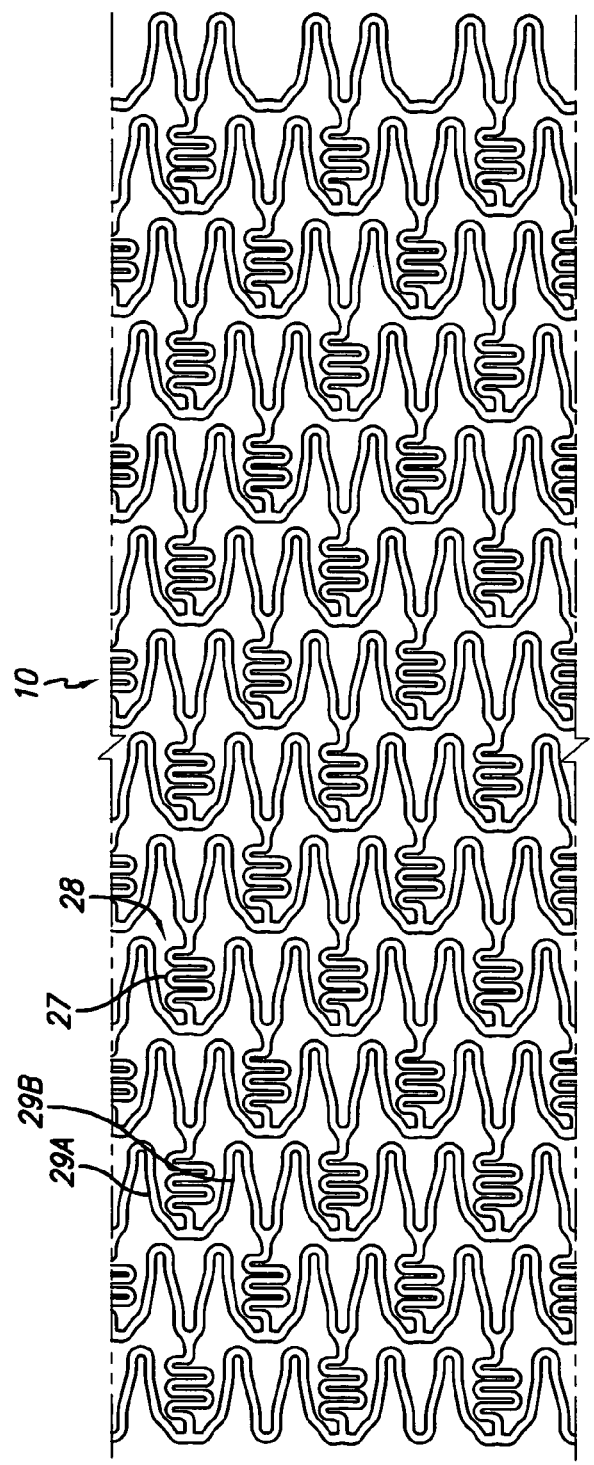
FIG. 4 is a plan view of a flattened prior art stent which illustrates the pattern of the stent shown in FIGS. 1-3.
Figure 5:
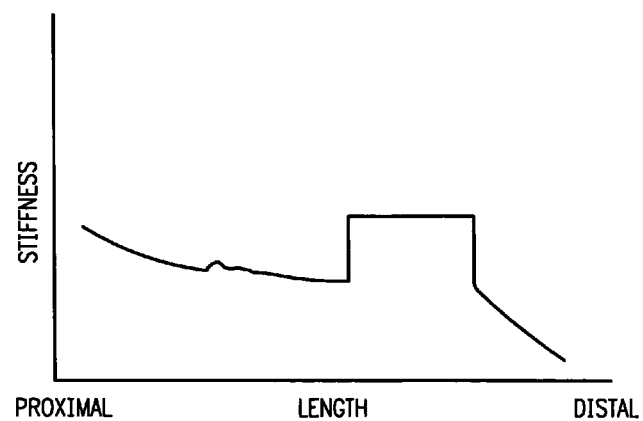
FIG. 5 is a plot showing, in very general terms, the stiffness profile of a prior art stent system, with the greatest stiffness being at the location of the stent.

As discussed previously with respect to FIG. 5, the design of FIGS. 6A-6C results in a stent which has a substantially constant bending stiffness across its length. It is desirable to design an alternative stent which has variable stiffness, with the least stiff portions being at ends of the stent and the greatest stiffness being in the center of the stent. This variable stiffness profile reduces the change in stiffness of the stent delivery system where the stent begins and ends.

Figure 7:
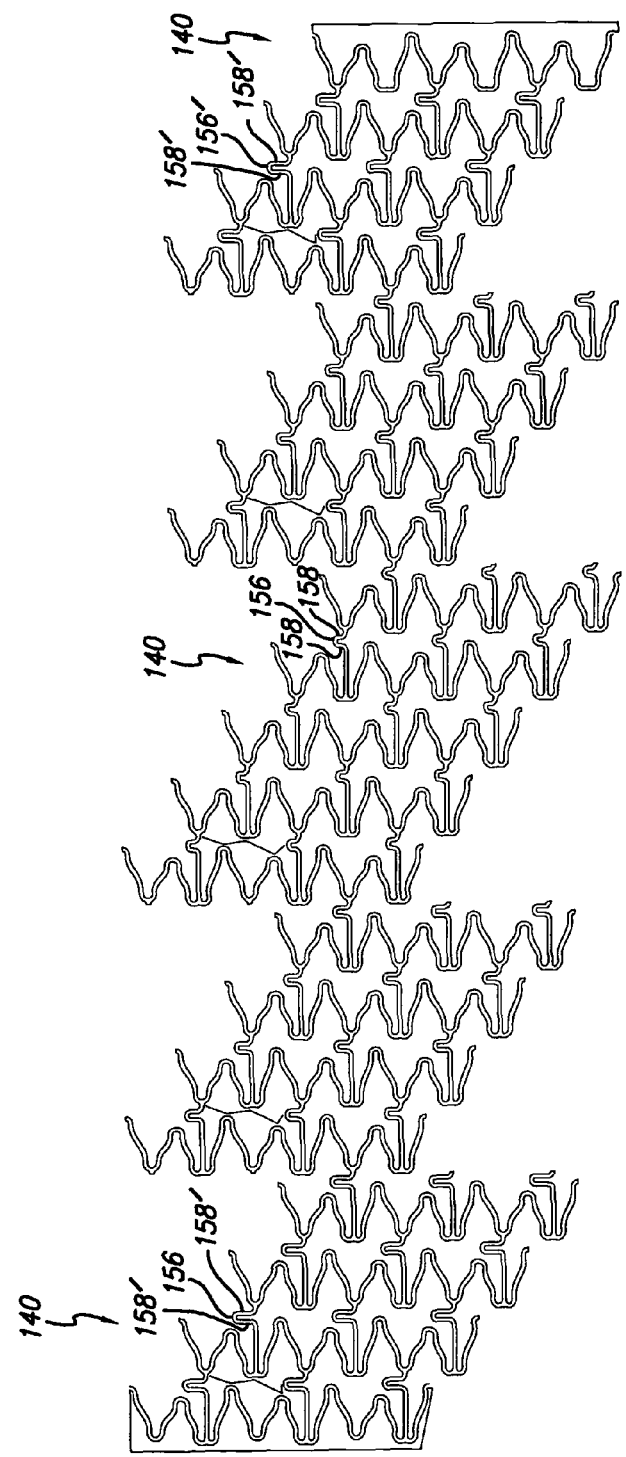
FIG. 7 is a plan view of a stent according to the present invention in which the diameter of the "U"-shaped members increases toward the ends of the stent.

Consistent with the present invention, FIG. 7 illustrates a stent pattern in which the undulating, generally "U-shaped" links 154 that connect the cylindrical rings 140 include straight portions 158 and curved portions 156. Unlike the links of FIGS. 6A-6C, the straight portions of the links gradually increase in length toward either end from the center of the stent. In FIG. 7, the straight portions 158' in the undulating links 154' at the ends of the stent are longer than the straight portions 158 toward the center of the stent. Consequently, the stent has greater bending flexibility at the ends than at the center. The change in length from portions 158 near the center to portions 158' toward the ends may be gradual.

Figure 8:
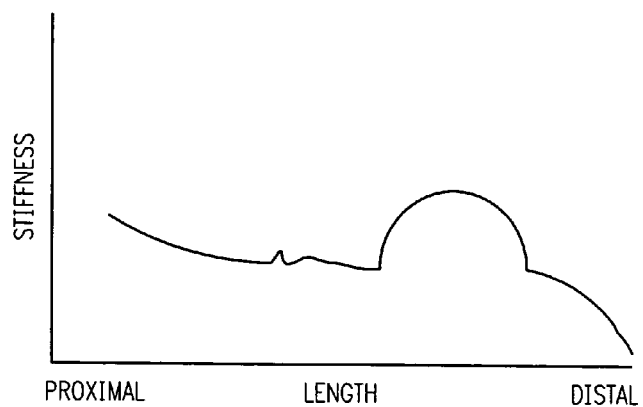
FIG. 8 is a generalized plot showing the relatively smooth transition in stiffness at either end of the stent along the stent delivery system.

FIG. 8 illustrates a generalized stiffness plot of a stent delivery system incorporating a stent having the design of FIG. 7. FIG. 8 illustrates that the transition in stiffness at either end of the stent is much more gradual than the similar transition illustrated in FIG. 5 with respect to prior art stents.

Figure 9:
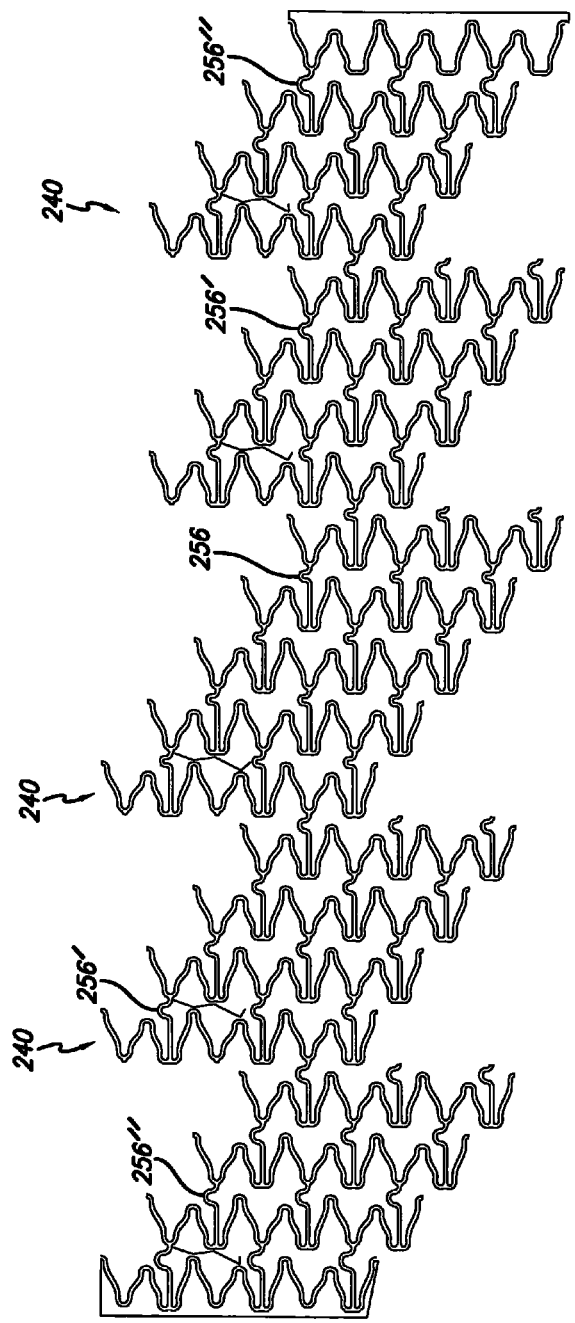
FIG. 9 is a plan view showing the pattern of another stent according to the present invention, in which links are of different thicknesses.

There are a number of alternative ways in which variable flexibility can be added to stents. In one embodiment that FIG. 9 illustrates, the links linking rings 240 have a curved portion. The radius of the curved portions 256 is greater toward the ends of the stent (note the larger radii of curves 256' and 256" toward the ends of the stent as compared to the smaller radius on the curve 256 toward the center of the stent.) The increase in radius from the curved link members at the center of the stent to the curved link members at the end of the stent may be gradual, to produce a gradually-changing stiffness profile. It should be noted that the curve need not have a constant radius of curvature, but can vary, for example, with varying curvature as in a golf club section shape, or an oval section shape.

Figure 10:
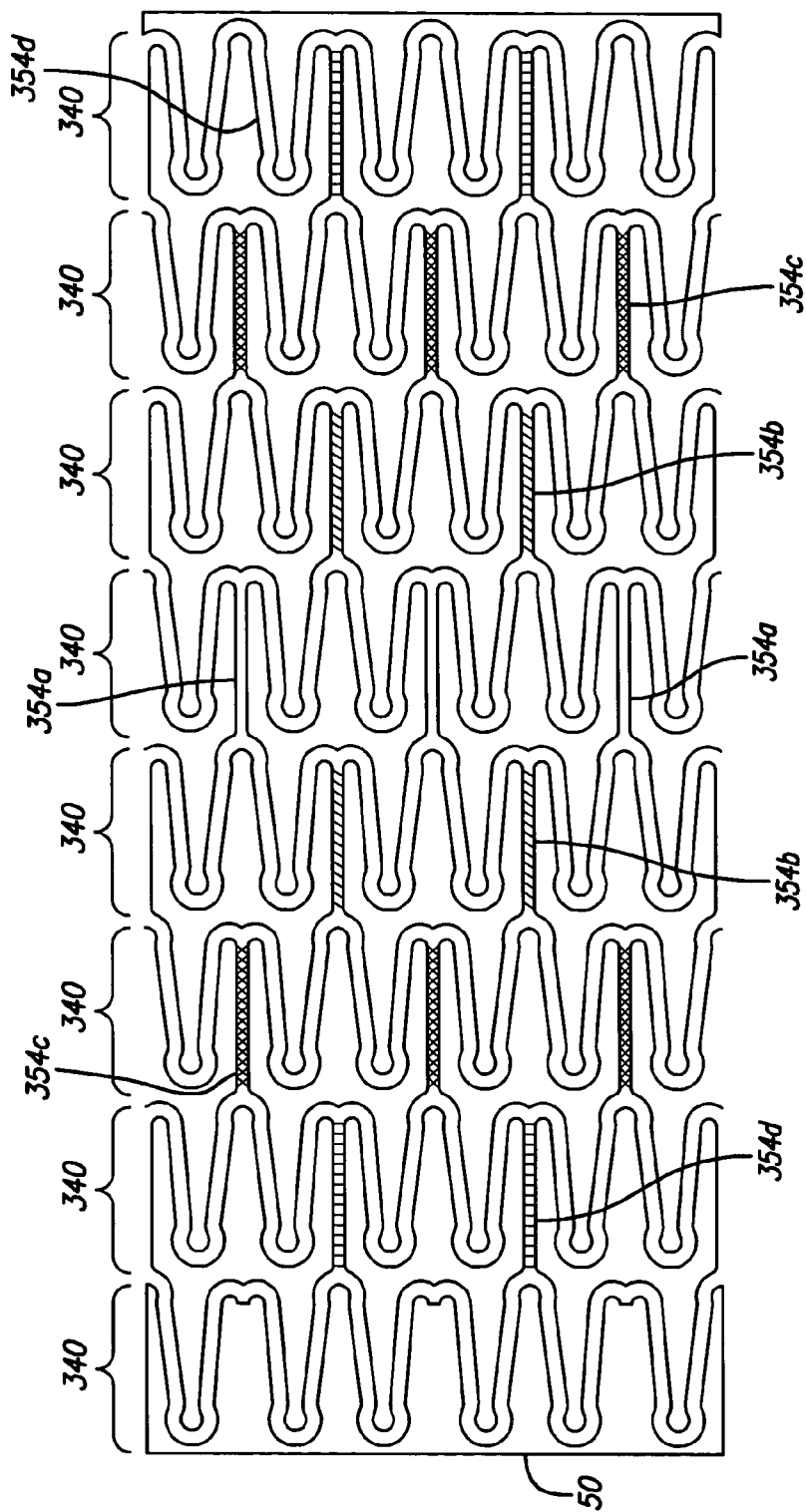
FIG. 10 is a plan view showing the pattern of another stent according to the present invention, in which links are made of different materials.

In another embodiment, the links are made of different materials. Referring to FIG. 10, the stent has rings 340 and links 354a-d. The links 354a at the center portion may be made of a material that is relatively stiff, whereas the links 354b-d toward the end portions may be made of a materials that are progressively less stiff. For example, the links at the center 354a may be made of a relatively stiff polymer, whereas the links at the end portions may be made of relatively more flexible polymers. The links may be attached to the rings by welding methods known in the art, for example.

Figure 11:
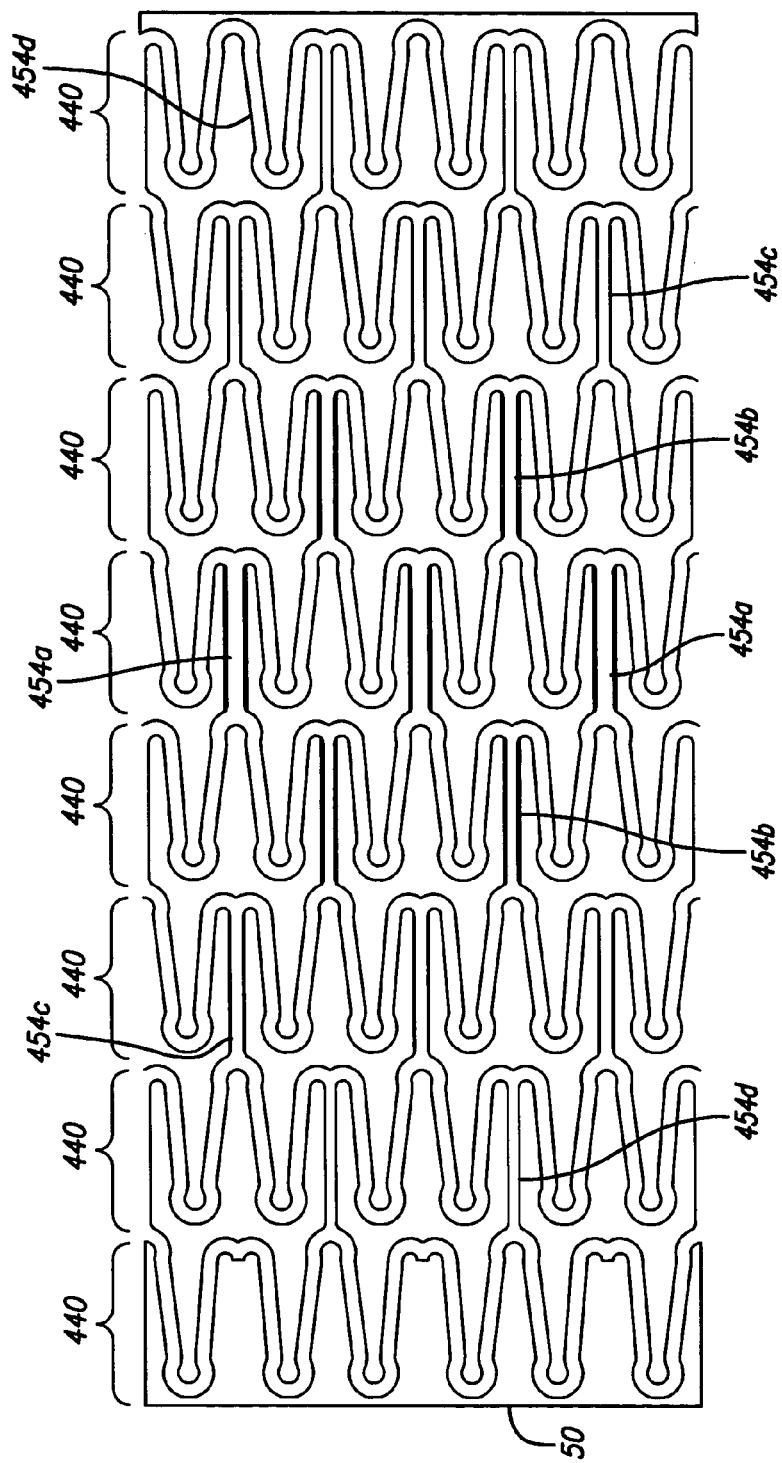
FIG. 11 is a plan view showing the pattern of another stent according to the present invention, in which links have decreasing thickness toward the ends of the stent.

In a further embodiment that FIG. 11 illustrates, links of different thicknesses can be used. The stent includes rings 440 and links 454a-d. The links 454a in the center portion of the stent may be thicker than the links 454b-d toward the end portions of the stent, which may gradually become thinner from the center of the stent outwardly toward the ends, thereby creating a stent stiffness profile in which the stent is more flexible at the ends than at the center.

Another embodiment includes multiple non-linearities in the links. That is, the links in the center portion of the stent may have fewer non-linearities than links at the end portions of the stent. For example, referring to the prior art stent of FIGS. 1-3, a stent according to the present invention may modify the undulating links 27 such that there are more curved members in links toward the ends than in links toward the center. That is, the number of non-linearities in the links increase toward the ends of the stent, thereby creating a stiffness profile in which the ends of the stent are more flexible than the center of the stent.

Figure 12:
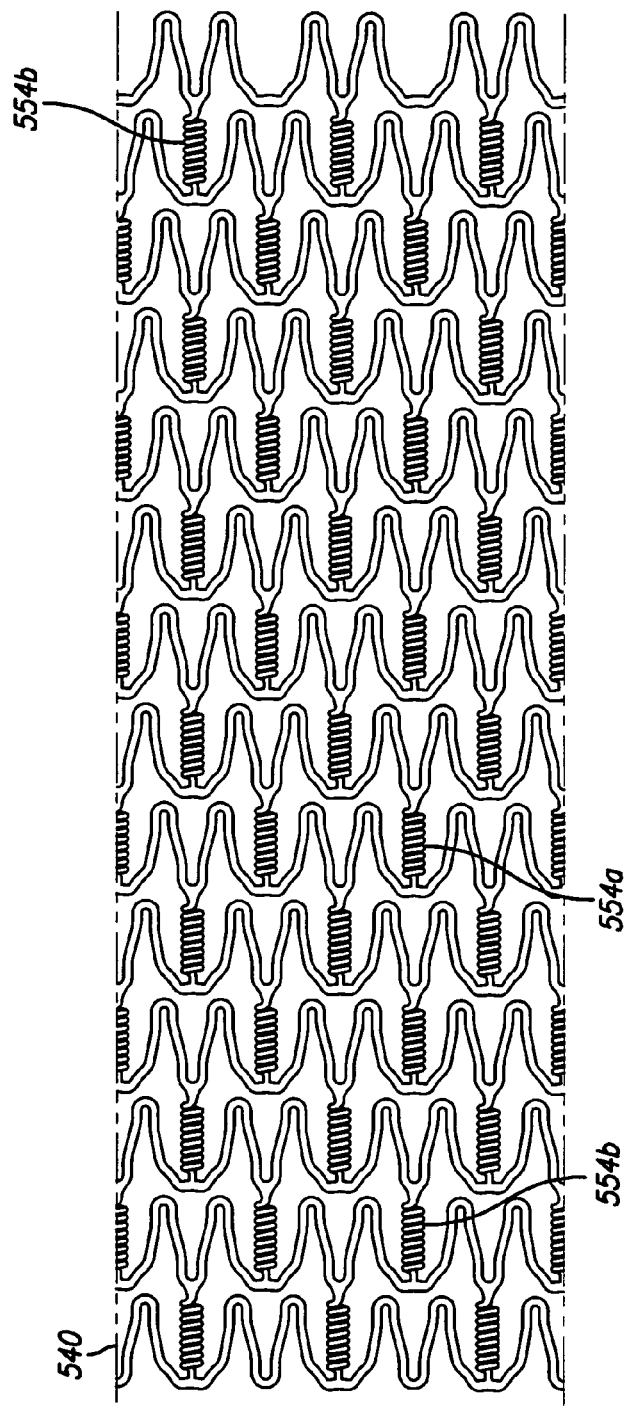
FIG. 12 is a plan view showing the pattern of another stent according to the present invention, in which the links are coils, with the coils toward the center of the stent being stiffer than coils toward the ends of the stent.

In yet another embodiment, the links may be coils of material. Referring to FIG. 12, rings 540 are connected by coils. The coils 554a at the center portion of the stent are stiffer than the coils 554b at the end portions of the stent. It should be noted that the coils need not be present in every ring. Similarly, an undulation need not be in every ring.

In any of the foregoing embodiments, it is noted that the change in stiffness may be gradual from the center to the end portions. Alternatively, the stiffness profile can be made relatively constant along the length of the stent, but suddenly more flexible at the ends. As a further alternative, one end of the stent may be made more stiff than the other end, if desired. These illustrative and non-limiting alternatives are provided merely to illustrate that many variations in the stiffness profile of the stent are possible within the scope of the invention.

The stent of the present invention can be mounted on a balloon catheter similar to that shown in the prior art device in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

The stent of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum. In accordance with the invention, it is preferred to cut the tubing in the desired pattern by means of a machine-controlled laser as is well known in the art.

Other methods of forming the stent of the present invention can be used, such as using different types of lasers; chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation, or display stress-induced martensit. These types of alloys are well known in the art and need not be further described here.

Importantly, a stent formed of shape memory alloys, whether the thermoelastic or the stress-induced martensite-type, can be delivered using a balloon catheter of the type described herein, or be delivered via a catheter without a balloon or a sheath catheter.

The stent of the invention also can be coated with a drug or therapeutic agent to assist in repair of the lumen and may be useful, for example, in reducing the likelihood of the development of restenosis. Further, it is well known that the stent (usually made from a metal) may require a primer material coating to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic drugs or pharmacologic compounds that may be loaded onto the stent pattern or into a polymeric coating on the stent, on a polymeric sleeve, or on individual filament strands on the stent, and delivered to the target site in the vasculature include taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D phe pro arg chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E 3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3 fatty acid), histamine antagonists, Lovastatin® (an inhibitor of HMG CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. The calculation of dosages, dosage rates and appropriate duration of treatment are previously known in the art. Furthermore, the therapeutic drugs or agents are loaded at desired concentration levels per methods well known in the art to render the device ready for implantation.

It should be understood that any reference in the specification or claims to a drug or therapeutic agent being coated on the stent is meant that one or more layers can be coated either directly on the stent or onto a primer material on the stent to which the drug or therapeutic agent readily attaches.

While the invention has been illustrated and described herein, in terms of its use as an intravascular stent, it will be apparent to those skilled in the art that the stent can be used in other body lumens. Further, particular sizes and dimensions, number of undulations or U-shaped portions or other nonlinearities per ring, materials used, and the like have been described herein and are provided as examples only. Different combinations of the above mentioned features can be made, and not every feature needs to be present in a particular embodiment. Not every feature needs to be present in each ring, for instance, and even in each ring, there can be combinations of features. For example, one section may have links that are wider, shorter, thicker and without undulations, whereas another section can have links that are narrower, longer, thinner and having undulations. Other modifications and improvements may be made without departing from the scope of the invention.

I claim:

1. A flexible stent for use in a body lumen, comprising:
a plurality of rings interconnected to form a stent having a first end portion, a center portion, and a second end portion, the center portion having a ring length and a strut width;
at least one link extending between each ring and an adjacent ring, wherein such link has a straight portion substantially parallel to a longitudinal axis of the stent and a curved portion extending transverse to the longitudinal axis, wherein such curved portion has a radius of curvature, and wherein the curved portion of the links in the center portion have a radius of curvature that is less than the radius of curvature of the curved portion of the links in at least one of the end portions such that said at least one end portion has more bending flexibility than the center portion.

2. A flexible stent as defined in claim 1, wherein the radius of curvature of the curved portions of the links in the center portion is less than the radius of curvature in the links of both the first and second end portions.

3. A flexible stent as defined in claim 1, wherein the radius of curvature of the curved portions of the links gradually decreases from at least one of the first and second end portions to the center portion.

4. A flexible stent as defined in claim 1, wherein the stent is coated with at least one of a drug and a therapeutic agent.

5. A flexible intravascular stent for use in a body lumen, comprising:
a plurality of cylindrical rings aligned along a common longitudinal axis and interconnected to form a stent having a first end portion, a center portion, and a second end portion, each cylindrical ring having a first delivery diameter and a second implanted diameter;
at least one link attaching each cylindrical ring to an adjacent cylindrical ring, the links being in the first end portion, the center portion, and the second end portion;
each link having a curved portion extending transverse to the stent longitudinal axis and wherein the curved portion of the links in the center portion have a diameter less than the diameter of the curved portion of the links in at least one of the end portions.

6. A flexible intravascular stent as defined in claim 5, wherein the curved portion of the links in the center portion have a diameter less than the diameter of the curved portion of the links of both the first and second end portions.

7. A flexible intravascular stent for use in a body lumen, comprising:
a plurality of cylindrical rings aligned along a common longitudinal axis and interconnected to form a stent having a first end portion, a center portion, and a second end portion, each cylindrical ring having a first delivery diameter and a second implanted diameter;
at least one link attaching each cylindrical ring to an adjacent cylindrical ring, the links comprising a curved portion extending transverse to the longitudinal axis and wherein the curved portion of the links in the center portion have a smaller curvature than the curved portion of the links in at least one of the end portions.

8. A flexible intravascular stent as defined in claim 7, wherein the links in the center portion have a curved portion with a smaller curvature than the curved portion of the links in both end portions.

9. A flexible intravascular stent as defined in claim 7, wherein the curvatures of the curved portions of the links gradually decrease from at least one of the end portions to the center portion.

10. A flexible intravascular stent as defined in claim 7, wherein the stent is coated with at least one of a drug and a therapeutic agent.

* * * * *